United States Patent
Bugatti

(10) Patent No.: US 7,449,197 B2
(45) Date of Patent: Nov. 11, 2008

(54) LIPOSOME FORMULATION OF 6,9-BIS[(2-AMINOETHYL)-AMINO]BENZO[G]ISOQUINOLINE-5, 10-DIONE DIMALEATE

(75) Inventor: Carlo Bugatti, Milan (IT)

(73) Assignee: Cell Therapeutics Europe S.r.l. (IT)

( * ) Notice: Subject to any disclaimer, the term of this patent is extended or adjusted under 35 U.S.C. 154(b) by 0 days.

(21) Appl. No.: 11/283,941

(22) Filed: Nov. 21, 2005

(65) Prior Publication Data

US 2006/0078607 A1 Apr. 13, 2006

Related U.S. Application Data

(63) Continuation of application No. 10/111,082, filed as application No. PCT/EP00/10303 on Oct. 19, 2000, now abandoned.

(30) Foreign Application Priority Data

Oct. 22, 1999 (IT) .............................. MI99A2219

(51) Int. Cl.
*A61K 9/127* (2006.01)

(52) U.S. Cl. ........................................... 424/450

(58) Field of Classification Search ................. 424/450
See application file for complete search history.

(56) References Cited

U.S. PATENT DOCUMENTS

| | | | |
|---|---|---|---|
| 4,797,285 A | | 1/1989 | Barenholz et al. |
| 5,213,804 A | * | 5/1993 | Martin et al. ............... 424/450 |
| 5,506,232 A | | 4/1996 | Spinelli et al. |
| 5,587,382 A | * | 12/1996 | Krapcho et al. ............. 514/290 |
| 5,605,703 A | * | 2/1997 | Lambiez et al. ............. 424/450 |
| 5,776,488 A | * | 7/1998 | Mori et al. .................. 424/450 |
| 5,795,589 A | * | 8/1998 | Mayer et al. ................. 424/450 |
| 6,726,924 B2 | * | 4/2004 | Keller ........................ 424/450 |

OTHER PUBLICATIONS

Borchmann et al, Blood (Nov. 15, 1998), vol. 92, No. 10, Suppl. 1, Part 1-2, pp. 234 B.*

* cited by examiner

*Primary Examiner*—Gollamudi Kishore
(74) *Attorney, Agent, or Firm*—Lerner, David, Littenberg, Krumholz & Mentlik, LLP

(57) ABSTRACT

A liposome pharmaceutical formulation of the compound of 6,9-bis-[(2-aminoethyl)-amino]benzo[g]isoquinoline-5,10-dione dimaleate, the method for the preparation and the use thereof.

6 Claims, 5 Drawing Sheets

DSC Analysis of PHOSPHOLIPON® 90

OLIVE OIL GASCHROMATOGRAM

PHOSPHOLIPON 90 GASCHROMATOGRAM

PHOSPHOLIPON 90H GASCHROMATOGRAM

DSC Analysis of PHOSPHOLIPON® 90H

LIPOSOME FORMULATION OF 6,9-BIS[(2-AMINOETHYL)-AMINO] BENZO[G]ISOQUINOLINE-5, 10-DIONE DIMALEATE

CROSS-REFERENCE TO RELATED APPLICATIONS

This application is a continuation of U.S. application Ser. No. 10/111,082, filed on Jun. 6, 2002, the disclosure of which is incorporated herein by reference. The present application is a national phase entry under 35 U.S.C. § 371 of International Application No. PCT/EP00/10303 filed Oct. 19, 2000, published in English, which claims priority from MI99A002219 filed Oct. 22, 1999, all of which are incorporated herein by reference.

BACKGROUND OF THE INVENTION

The present invention relates to a liposome pharmaceutical formulation of the compound 6,9-bis-[(2-aminoethyl)amino] benzo[g]isoquinoline-5,10-dione dimaleate (BBR 2778).

Liposomes are aqueous dispersions of natural and/or synthetic phospholipids (biocompatible and biodegradable) organized in one or more bilayers. When phospholipids are hydrated in aqueous medium, they spontaneously form colloidal micro-particles or carriers, usually of 0.05-5.0 µm of diameter. Liposome particle size ranges from 0.025 µm to 2.5 µm, depending on their structure which can be a single or multiple bilayer structure. The vesicle size is a critical parameter to the determination of liposomes half-life and it affects the volume of the encapsulable medicament.

Liposomes can be classified according to their composition in natural and/or synthetic phospholipids (phosphor-sphingolipids) and their bilayer can further contain other components, such as cholesterol and lipid-conjugated hydrophilic polymers. Depending on their size and number of bilayers, liposomes can also be divided into the following categories: (a) multilamellar vesicles (MLV), (b) large unilamellar vesicles (LUV), (c) small unilamellar vesicles (SUV), (d) multivesicle vesicles (MVV), (e) oligolamellar vesicles (OLV).

The chemical-physical properties of phospholipids which constitute liposomes, such as membrane fluidity, charge density, steric hindrance and permeability, affect the interaction between liposomes and blood components, tissues and cells.

Liposomes are recognizedly to be potentially valuable carriers for medicaments. The capability of liposomes of containing, carrying and releasing medicaments has lead to a number of clinical applications. The simplest use of liposomes in the pharmaceutical field is as non-toxic carriers for insoluble drugs. More complex applications involve the use of liposomes as "reservoirs" for the protracted release of drugs or for the localization of the drug, to either avoid or reach a specific tissue. Drugs in liposome form gave favorable results in the treatment and prevention of a number of diseases, such as in antimicrobial therapy, in anticancer therapy, as adjuvants in vaccines, in hormone and enzyme therapies, in diagnostic techniques and in the treatment of skin and eyes disease. The drugs used in the treatment of diseases such as cancer usually have a restricted therapeutic index and can be highly toxic for normal tissues. A liposome formulation can improve the therapeutic index, modifying the drug biodistribution. Some experiments with liposome-encapsulated anthracyclines with extended plasma half-life have shown a reduction in cardiotoxicity and a better survival of the animals compared with controls, which had been given the free drug.

In the case of doxorubicin, an anthraquinone antitumor drug, the use of liposome formulations proved to be effective in reducing toxicity. Doxorubicin most dangerous side-effect is progressive, irreversible heart damage. Liposome-encapsulated doxorubicin showed lower toxicity while maintaining its therapeutic efficacy. U.S. Pat. Nos. 4,797,285, 4,898,735 and 5,043,166 disclose doxorubicin/liposome formulations and the use thereof in the treatment of cancer.

SUMMARY OF THE INVENTION

The compound BBR 2778 is an anthraquinone antitumor drug with antitumor activity and reduced cardiotoxicity, having the following formula:

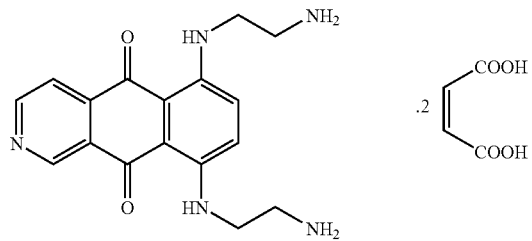

The complete description of the compound BBR 2778 is reported in U.S. Pat. Nos. 5,587,382, 5,717,099, 5,506,232, 5,616,709 and in J. Med. Chem., 1994, Vol. 37, 828-837.

After i.v. administration of doses of 40 or 60 mg/kg of BBR 2778 as a bolus to CD1 mice, death of some animals is observed either during or immediately after the treatment.

Such sudden deaths are supposedly due to one of the following factors related to the use of BBR 2778: thrombogenic activity; alteration of hemocoagulation parameters, with consequent formation of disseminated intravascular coagulations; induction of anaphylactic shock; direct toxic effect on central nervous system; anhythmogenic activity; electrolytic unbalance. This dose-dependant phenomenon decreases as the injection rate decreases (0.1 ml/min, 7-8 minutes per injection) and also through intraperitoneal administration.

The problem underlying the present invention was therefore to find a suitable formulation of compound BBR 2778 to overcome the disadvantages mentioned above, specifically the sudden deaths observed after bolus administration of the active ingredient. It has surprisingly been found that a BBR 2778 liposome formulation characterized by a particular composition, successfully solves said problem.

DETAILED DESCRIPTION OF THE INVENTION

Figure 1:
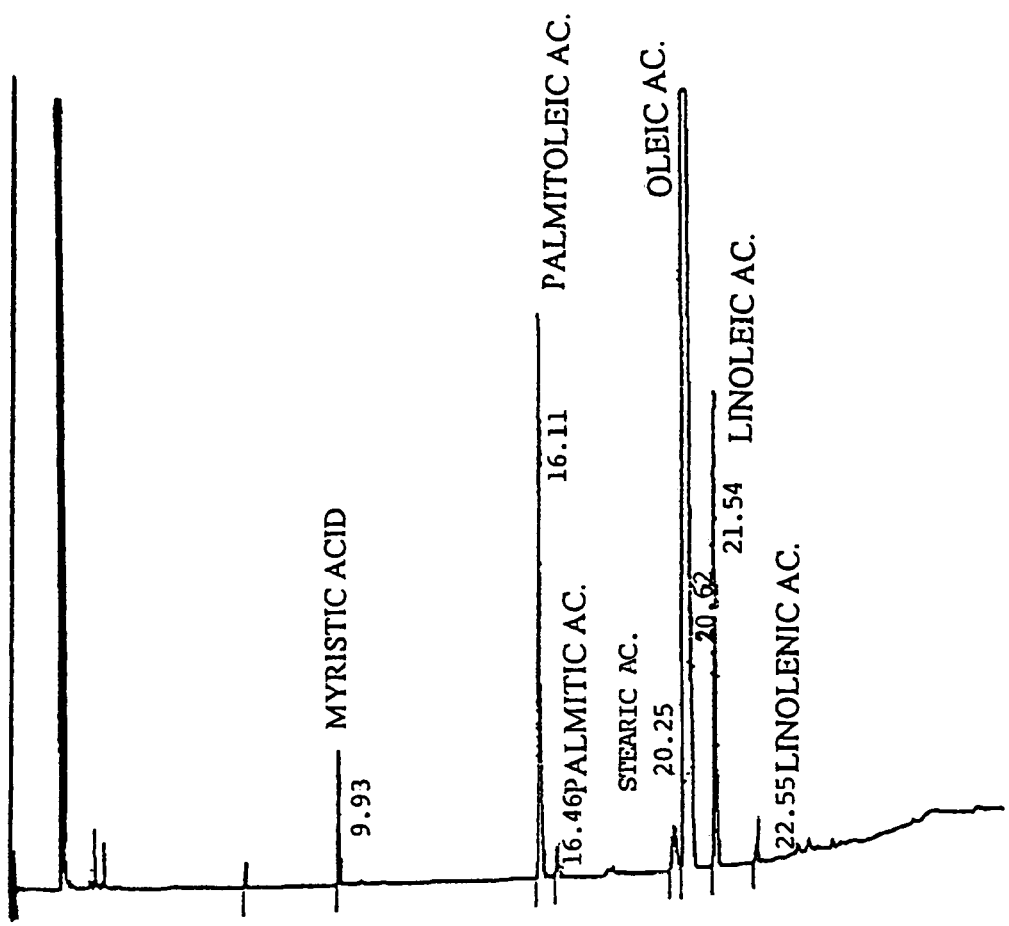
FIG. 1 is a gaschromatogram of olive oil, the standard.

Therefore, the invention provides a liposome formulation of compound BBR 2778 consisting of liposomes comprising phosphatidylcholine, cholesterol and BBR 2778, in a cholesterol/phospholipide 1:2 to 1:7 weight ratio and in a BBR 2778/phospholipide 1:4 to 1:25 weight ratio. Phosphatidylcholine preferably includes residues of fatty acids selected from palmitic, oleic, linoleic, gamma-linoleic, linolenic and stearic acids, and the liposome is formed by a mixture of hydrogenated and non-hydrogenated phosphatidylcholines, having the fatty acids composition indicated, in a 1:2 to 2:1 ratio, more preferably said mixture consists of hydrogenated phosphatidylcholine having melting point of 120° C. and crystallization point of 90° C., and non-hydrogenated phosphatidylcholine having a thermogram as reported in FIG. 5. The hydrogenated and non-hydrogenated phosphatidylcholines, having the above-indicated composition, are commercially available respectively under the name PHOSPHOLIPON® 90 H and PHOSPHOLIPON® 90.

Preferably, the composition of the invention comprises, in addition to the above-mentioned components, charged compounds such as stearylamine and dicetylphosphate. The addition of said components gives liposomes a surface charge which induces their mutual repulsion thus preventing them from collapsing. The phospholipid mixture can also contain sodium dodecylsulfate, cremophor RH60, alpha-tocopherol phosphate and calcium acetate. Furthermore, small fractions (5-19 mol %) of compounds with hydrophilic groups such as monosialoganglioside, hydrogenated phosphatidyl inositol and lipid-conjugated polyethylene glycols (PEGDSPE), can be included in the membrane bilayer to reduce the interaction between liposomes and cells and blood components.

The liposome formulations according to the invention were tested in vivo for the antitumor activity and toxicity. P388 murine leukemia was used as tumor model. In particular, the inhibitory activity on sudden deaths was evaluated compared with the control group, which was administered with a formulation of the free drug. Details are reported in the Examples. The results of the tests prove that the liposome formulations of the invention cause a remarkable improvement of the mean survival time and a marked decrease in toxicity. Furthermore, sudden death is no longer observed.

In conclusion, it can therefore be stated that the formulations of the invention maintain the antitumor activity without inducing sudden death, which is observed in the case of the free drug or other conventional formulations of the active ingredient.

The following examples illustrate the invention in greater detail.

EXAMPLE 1

Purification of Lecithin to Phosphatidylcholine

The main source of lecithin are vegetable oils from soybean, cotton, sunflower and colza seeds or from animal tissues (eggs). Soy and egg lecithins are the most important in terms of produced amounts. Soy beans are subjected to extraction with hexane to obtain crude lecithin of semisolid consistence which contains:

52% of phospholipids, 35% of oils and fats, 10% of glycolipids and sugars, 2% of unsaponifiables and 1% of water.

Fatty acids are extracted from the crude lecithin to obtain a fine or granular lecithin powder which is further extracted with ethanol and fractionated to obtain purer lecithins with higher phosphatidylcholine contents.

Crude lecithin was also purified by using a single process for the industrial production of phosphatidylcholine by extraction with acetone, as disclosed in U.S. Pat. No. 5,442,276.

| Purification of crude lecithin |
|---|
| CRUDE LECITHIN |
| EXTRACTION (ethanol) CHROMATOGRAPHY (Silicagel) PHOSPHOLIPON 80 |
| CHROMATOGRAPHY (aluminum oxide) PHOSPHOLIN 90 |
| hydrogenation PHOSPHOLIN 90H |

PHOSPHOLIPON® 90H (PHO 90H) was obtained by hydrogenation of PHOSPHOLIPON® 90 (PHO 90).

The two commercial phospholipids (Rhone—Poulenc Rorer) have the following characteristics:
PHOSPHOLIPON® 90:
Peroxides index: max. 5
Acid value: max. 0.5
Ethanol: max. 0.5%
Water max. 1.5%
Form: yellow pasty solid
Addition of d,l α-tocopherol min. 0.1%.
PHOSPHOLIPON® 90H
Iodine number: max. 1
Water: max. 2.0%
Phase transition temperature of the 20% dispersion in $H_2O$ about 54° C.
Form: white crystalline solid.

Glycerol 1- and 2-positions in the phosphatidylcholine molecule are esterified with fatty acids such as palmitic, oleic, linoleic, linolenic and stearic acids.

EXAMPLE 2

Chromatographic Analysis of the Phospholipids

The fatty acids composition of the phosphatidylcholine samples in both quantitative and qualitative terms was determined by GLC analysis. Fatty acids in the phospholipid samples were detected and dosed using both pure fatty acids methyl esters (Carlo Erba) and standard olive oil.

Saponification of the sample: 50 mg of product were placed in a test-tube and added with 3 ml of 1N sodium hydroxide (Baker). The t-tube was tightly sealed and place in a suitable oven at 110° C. for one hour. After cooling to room temperature, the sample was acidified with 2N hydrochloric acid (Baker) and extracted with 10 ml of a n-hexane/ethyl acetate 90/10 (Merck) mixture. The organic solvent was removed under mild nitrogen stream.

Figure 2:
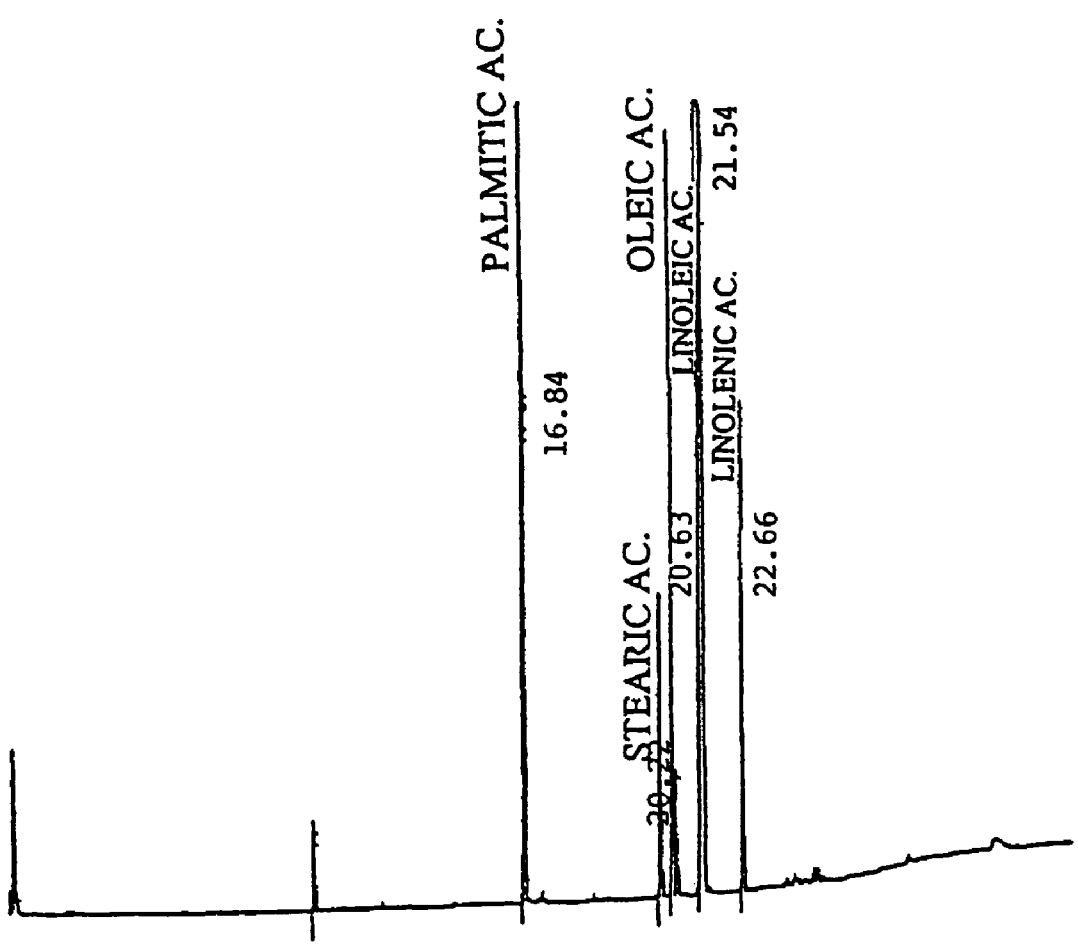
FIG. 2 is a gaschromatogram of PHOSPHOLIPON 90.
Figure 3:
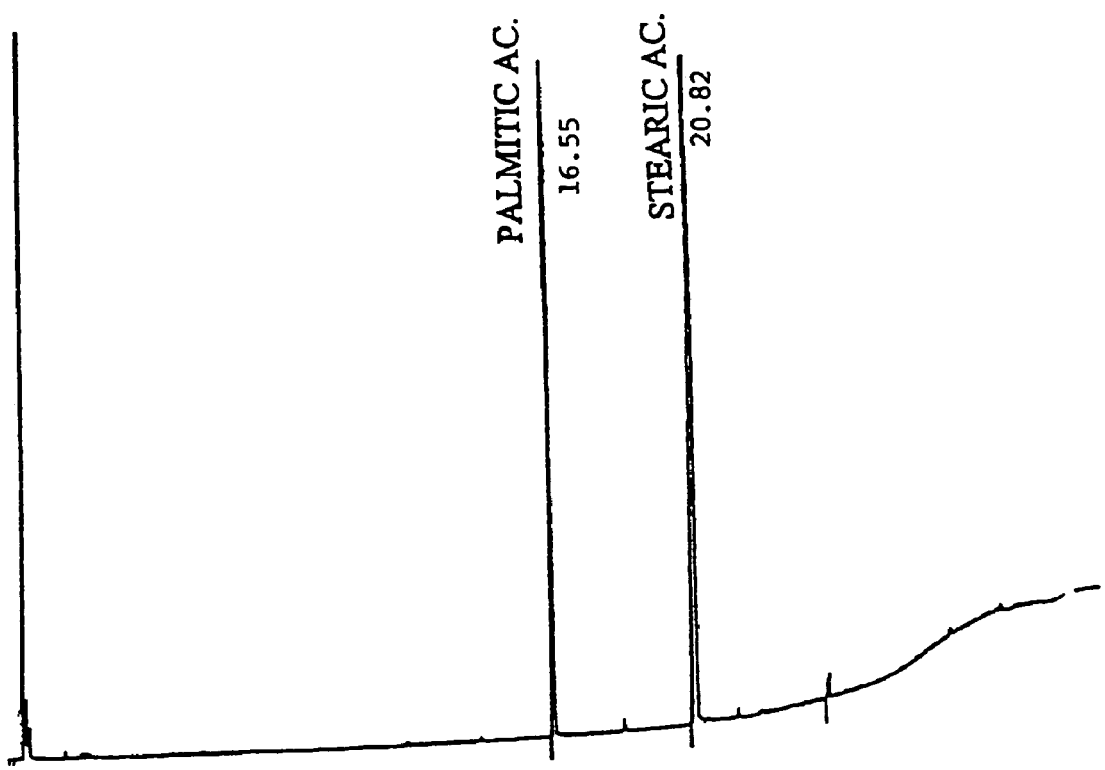
FIG. 3 is a gaschromatogram of PHOSPHOLIPON 90H.

Esterification of the samples: the organic phase was removed from the t-tube, 1 ml of $BF_3$ in methanol was added, the t-tube was tightly sealed and kept for 1 hour at 100° C. After cooling to room temperature, the sample was added with 5 ml of distilled water and extracted twice with 5 ml each of the n-hexane/ethyl acetate 90/10 mixture. 1 µl of the organic phase was dried over $Na_2SO_4$ then injected in the gaschromatographic device.
Operative Conditions
Gaschromatograph: Mega 5300 Carlo Erba
Column: Megawax, length 30 m, i.d. 0.32 mm, f.t. 0.25 µm
Carrier: helium sp 45 cm/sec Injector: split 1/100 a 250° C.
Detector: F.I.D. at 280° C.
Oven: 120° C. for 1 min
Final temperature: 250° C., with 5° C./min thermal increases FIGS. 1-3 respectively show the gaschromatograms of the standard, of PHO 90 and of PHO 90H.

Table 1 shows the acids percentages in the analyzed lipids.

TABLE 1

| Fatty acids | Phospholipon 90 | Phospholipon 90H |
|---|---|---|
| Stearic | 4.13 | 85 |
| Palmitic | 14.21 | 14 |
| Oleic | 9.84 | — |
| Linoleic | 64.44 | — |
| Gamma linoleic | 1.50 | — |
| Linolenic | 5.88 | — |

EXAMPLE 3

Phospholipids Thermal Analysis

Commercial phospholipids PHO 90 and PHO 90H, both alone and in mixture, were analyzed by DSC.

Samples were prepared as follows: 500 mg of PHO 90 were dissolved in 10 ml of dichloromethane+1 ml of MeOH (S1); 500 mg of PHO 90H were dissolved in 10 ml of dichloromethane+1 ml of MeOH ($S_2$).

Sample 1: 2 ml of $S_1$
Sample 2: 2 ml of $S_2$
Sample 3: 0.5 ml of $S_1$+1.5 ml of $S_2$
Sample 4: 1 ml of $S_2$+1 ml of $S_2$
Sample 5: 1.5 ml of $S_1$+0.5 ml of $S_2$ Samples were dried under nitrogen stream and mild heating, then analyzed by DSC. The analysis was performed with a Mettler DSC 20, heating to 200° C. with a 3° C./minute gradient, then allowing the sample to cool.

Figure 4:
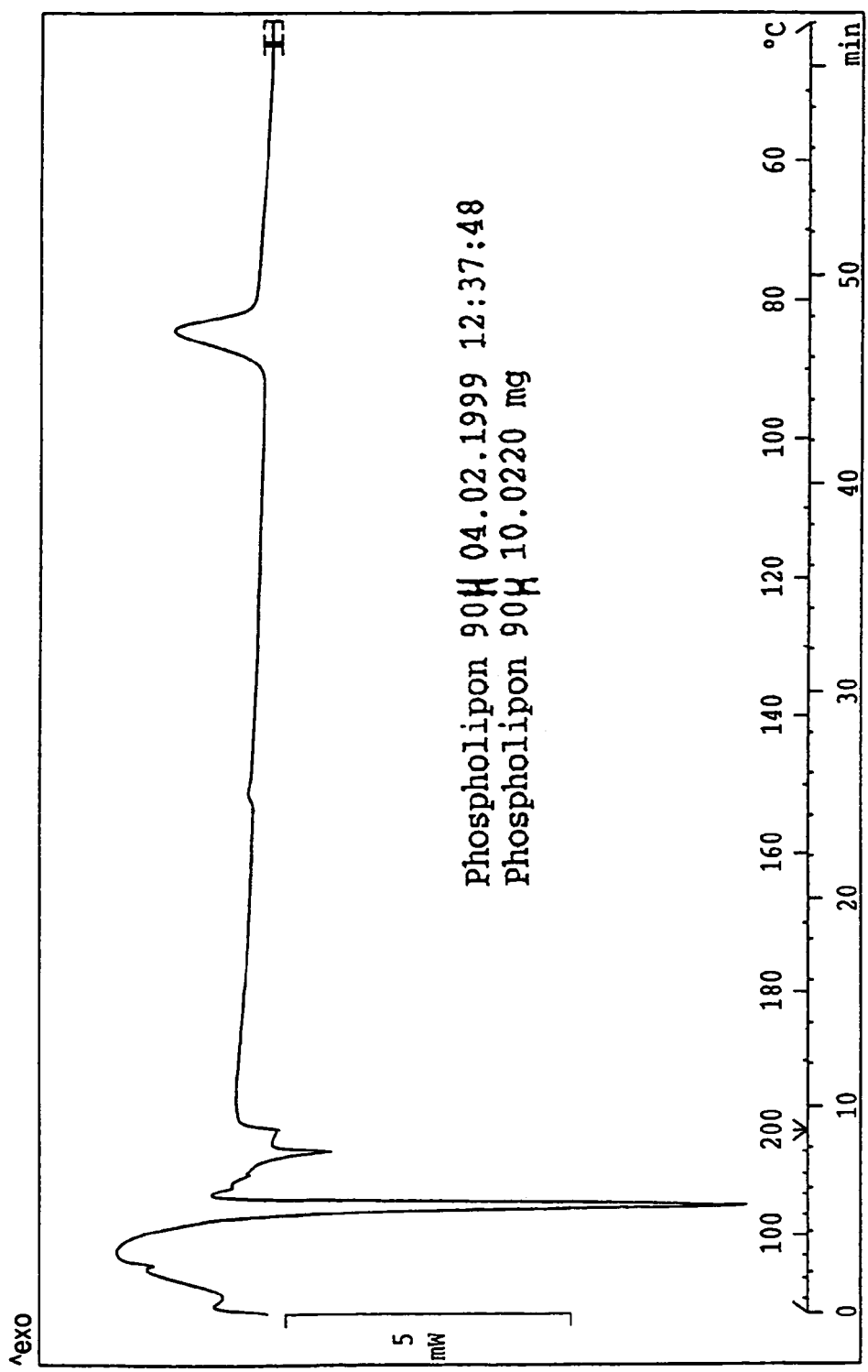
FIG. 4 is a thermogram of PHOSPHOLIPON 90H.
Figure 5:
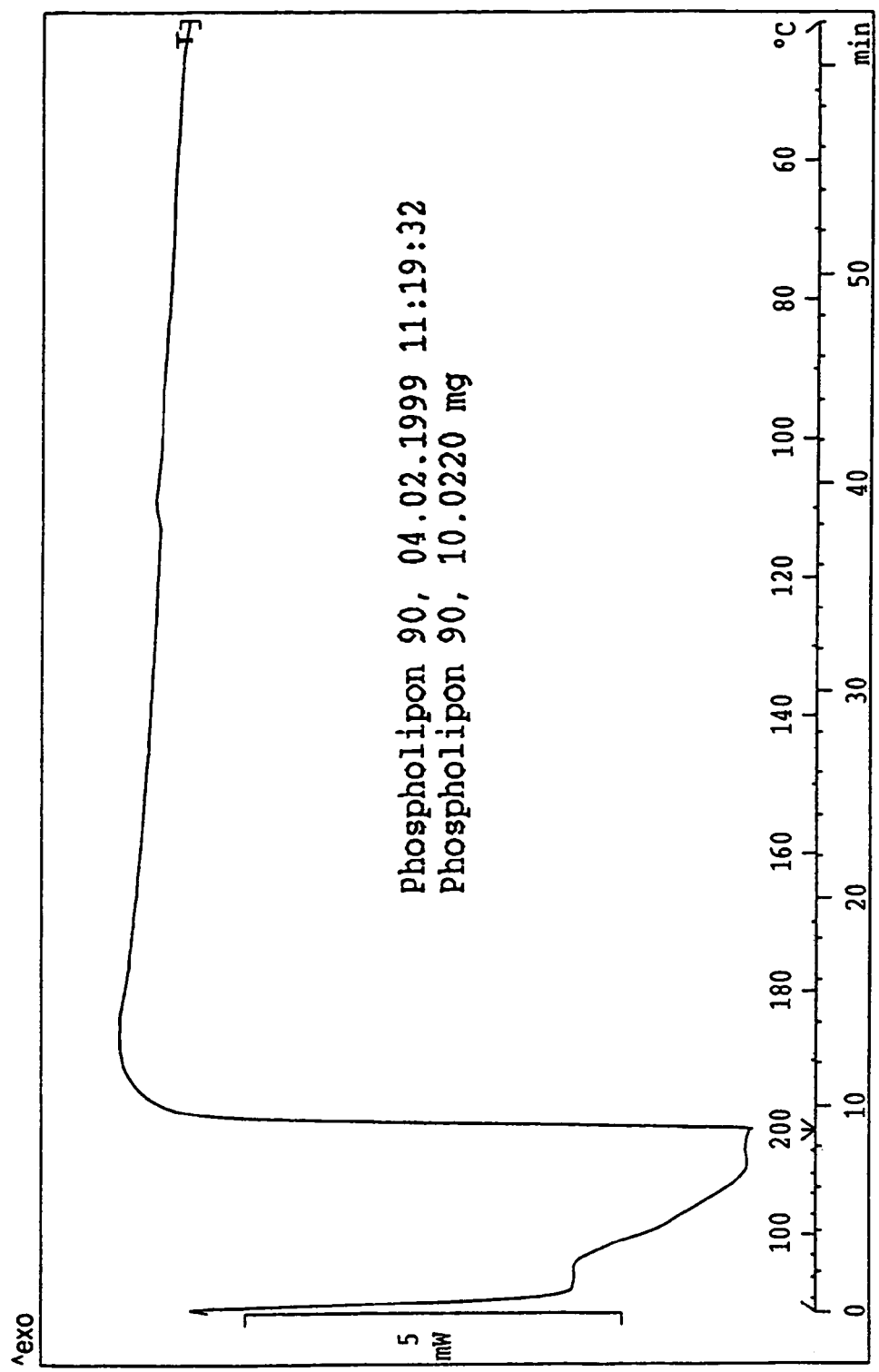
FIG. 5 is a thermogram of PHOSPHOLIPON 90.

FIGS. 4-5 report the thermograms of the two phospholipids. As it can be observed in FIG. 4, PHO 90H has marked, well defined melting point at 120° C., and crystallization point at 90° C.

As far as PHO 90 is concerned, FIG. 5 shows that this is not a crystalline powder, but a pasty mass, therefore, as is the case with all fats, it has no well-defined melting point, but a softening point, which is the temperature at which the fat starts flowing and a clearness point, which is the temperature at which the fat is completely clear.

This is confirmed by the thermogram of PHO 90 wherein a broad band corresponding to the softening point is observed instead of a defined peak as is the case with PHO 90H thermogram.

As for the thermograms of the mixtures, a decrease in the crystallization point is observed at lower temperatures, which further decreases from the PHO 90H:PHO 90 2:1 mixture to the 1:1 one, to finally completely disappear in the PHO 90H:PHO 90 1:2 mixture, wherein the PHO 90 behavior prevails.

EXAMPLE 4

Preparation of the Liposome Formulation 3.6 g of PHO 90, 1.8 g of PHO 90H (2:1 ratio) and 0.52 g of cholesterol were placed in a 500 ml round-bottom flask and added with 50 ml of dichloromethane. The mixture was sonicated for about 10 minutes to promote solubilization. The resulting solution was evaporated to dryness in rotary film evaporator (Rotavapor) at 40° C. under vacuum and with slight rotation until obtaining a homogeneous phospholipid film.

The resulting phospholipid film was cooled, then added with a solution of BBR 2778 prepared by dissolving 300 mg of BBR 2278 in 60 ml of water/propylene 5 glycol 60/40 and filtering through a 0.22 μm filter, and 10 ml of glass beads of 2 mm mean diameter. The round-bottom flask connected with the rotavapor was left under slow motion overnight (15 hours, 300 revolutions/min) at room temperature and pressure until complete rehydration. Table 2 reports the analysis of the resulting BBR 2778 formulation.

TABLE 2

| Formulation of BBR 2778 | |
|---|---|
| % ENCAPSULATED in liposomes | 85.82 |
| Total concentration of BBR 2778 (mg/ml) | 4.76 |
| % liposomes of size ≦0.22 μm | 63.53 |

EXAMPLE 5

Evaluation of the Antitumor Activity of BBR 2778 Liposomes

Animals: mice were provided by Charles River Breeding Laboratories (Calco, Como, Italy); they were male mice of 6-8 weeks under standard housing conditions.

Formulations: BBR 2778 dissolved and diluted in sterile water just before administration of 10 mg/kg to mice was used as reference. The liposome formulation of Example 4 was used.

Tumor model: P388 murine leukemia, provided by NCI Frederick Cancer Facility (USA) is maintained through a series of intraperitoneal transplants in DBA2 mice. Mice were transplanted with $10^6$ cells/mouse of P388 leukemia, the liposome compound and the reference standard were administered i.v. at days 1, 4, 7 after tumor transplant.

The antitumor activity was determined as percent increase in the survival time of mice, expressed by the T/C % ratio of the mean survival time (TMS) of the treated group (T) to the mean survival time of the control group (C):

$$T/C\% = \frac{TMS \text{ treated animals}}{TMS \text{ control animals}} \times 100$$

Table 3 reports the results of the antitumor activity of BBR 2778 in the tested formulation.

TABLE 3

| Compound | Dose (mg/kg/day) | T/C % | TOX* | Sudden deaths |
|---|---|---|---|---|
| Controls | | 100 | 0/9 | — |
| BBR 2778 solution | 18 | 199** | 1/56 | — |
|  | 27 | 226** | 9/71 | — |
|  | 40 | 159** | 32/53 | 2/53 |
|  | 60 | 36** | 23/32 | 2/32 |
| Formulation Example 4 | Carrier | 100 | 0/8 | |
|  | 18 | 187; 194 | 0/17 | |
|  | 27 | 225; 244 | 0/17 | |

TABLE 3-continued

| Compound | Dose (mg/kg/day) | T/C % | TOX* | Sudden deaths |
|---|---|---|---|---|
| | 40 | 287; 250 | | 2/16 |
| | 60 | 87; 44 | | 17/17 |

*Number of toxic deaths/total number of mice
**mean value of more tests

Comparison between the formulation of Example 4 and the BBR 2778 solution clearly evidences the disappearance of sudden deaths in the mice administered the liposome formulation. Analysis of each single dose administered shows variations both in terms of T/C % and of toxicity between the liposome formulation and the solution formulation; at doses of 18 mg/kg and 27 mg/kg no substantial differences are observed in terms of T/C %, whereas in terms of toxicity this is observed only after treatment with non-encapsulated BBR 2778.

The formulation of the invention compared with the BBR 2778 in solution at a dose of 40 mg/kg induces a remarkable improvement of the mean survival time:
287, 250 and 159 respectively and a marked decrease in toxicity (12% and 60.4% respectively). The dose of 60 mg/kg is toxic with both formulations.

It can therefore be stated that administration of the liposome formulation of BBR 2778 of the invention induces no sudden death, as well as a reduction of toxicity.

As for the antitumor activity, the results from the tests of BBR 2778 in solution are confirmed, even with remarkable increases in T/C % at some dosages.

The invention claimed is:

1. A liposome formulation comprising phosphatidylcholine, cholesterol, and compound 6,9-bis-[(2-aminoethyl)-amino]benzo[g]isoquinoline-5,10-dione dimaleate (BBR 2778) of formula:

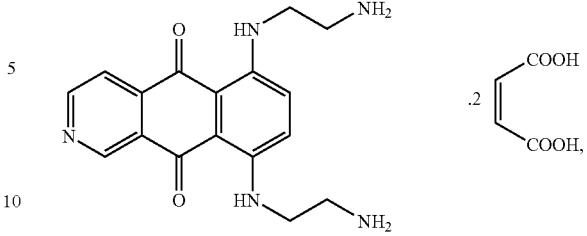

in a weight ratio of said cholesterol to said phosphatidylcholine of 1:2 to 1:7 and a weight ratio of said BBR 2778 to phosphatidylcholine of 1:4 to 1:25.

2. The liposome formulation of claim 1, wherein said phosphatidylcholine comprises residues of fatty acids selected from the group consisting of palmitic, oleic, linoleic, gamma linoleic, linoleic and stearic acids.

3. The liposome formulation of claim 1, wherein said phosphatidylcholine is a mixture of the hydrogenated and non-hydrogenated forms of phosphatidylcholine in a 1:2 to 2:1 weight ratio.

4. The liposome formulation of claim 1, wherein said liposome formulation further comprises stearylamine and/or dicetyl phosphate.

5. A method of providing antitumor activity with reduced toxicity comprising administering the liposome formulation of claim 1 to an animal.

6. The liposome formulation of claim 3, wherein said hydrogenated form of phosphatidylcholine has a melting point of 120° C. and crystallization point of 90° C., and said non-hydrogenated form has softening melting and crystallization points.

* * * * *